(12) United States Patent
Friedman et al.

(10) Patent No.: US 11,224,375 B2
(45) Date of Patent: Jan. 18, 2022

(54) SYSTEMS AND METHODS FOR FETAL MONITORING

(71) Applicant: Mayo Foundation for Medical Education and Research, Rochester, MN (US)

(72) Inventors: Paul A. Friedman, Rochester, MN (US); Dorothy J. Ladewig, Mazeppa, MN (US); Itzhak Zachi Attia, Rochester, MN (US); Kyle D. Traynor, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 218 days.

(21) Appl. No.: 16/489,600

(22) PCT Filed: Feb. 23, 2018

(86) PCT No.: PCT/US2018/019360
§ 371 (c)(1),
(2) Date: Aug. 28, 2019

(87) PCT Pub. No.: WO2018/160446
PCT Pub. Date: Sep. 7, 2018

(65) Prior Publication Data
US 2020/0113470 A1 Apr. 16, 2020

Related U.S. Application Data

(60) Provisional application No. 62/464,783, filed on Feb. 28, 2017.

(51) Int. Cl.
*A61B 5/00* (2006.01)
*A61B 5/344* (2021.01)
(Continued)

(52) U.S. Cl.
CPC ............ *A61B 5/344* (2021.01); *A61B 5/0006* (2013.01); *A61B 5/332* (2021.01); *A61B 5/349* (2021.01);
(Continued)

(58) Field of Classification Search
CPC ... A61B 5/0006; A61B 5/02411; A61B 5/318; A61B 5/332; A61B 5/339; A61B 5/344;
(Continued)

(56) References Cited

U.S. PATENT DOCUMENTS

| | | |
|---|---|---|
| 5,123,420 A | 6/1992 | Paret |
| 5,184,619 A | 2/1993 | Austin |

(Continued)

FOREIGN PATENT DOCUMENTS

| | | |
|---|---|---|
| WO | WO 2014/207484 | 12/2014 |
| WO | WO 2016/102971 | 6/2016 |
| WO | WO 2016/147051 | 9/2016 |

OTHER PUBLICATIONS

Ashish et al., "Inadequate Fetal Heart Rate Monitoring and Poor Use of Partogram Associated With Intrapartum Stillbirth: A Case-Referent Study in Nepal," BMC Pregnancy and Childbirth, 16:233, Aug. 2016.

(Continued)

*Primary Examiner* — George Manuel
(74) *Attorney, Agent, or Firm* — Fish & Richardson P.C.

(57) ABSTRACT

A system obtains a maternal electrocardiogram (ECG) signal that represents an ECG of a pregnant mother during a first time interval. The system further obtains a mixed maternal-fetal ECG signal that represents a combined ECG of the mother and her fetus during the first time interval; processes the maternal ECG signal and the mixed maternal-fetal ECG signal to generate a fetal ECG signal that represents the ECG of the fetus during the time interval, the fetal ECG signal (Continued)

substantially excluding the maternal ECG signal; and provides an output based on the fetal ECG signal.

17 Claims, 12 Drawing Sheets

(51) Int. Cl.
    *A61B 5/332*     (2021.01)
    *A61B 5/349*     (2021.01)
    *A61B 5/024*     (2006.01)
    *A61B 5/339*     (2021.01)

(52) U.S. Cl.
    CPC ......... *A61B 5/6898* (2013.01); *A61B 5/02411* (2013.01); *A61B 5/339* (2021.01); *A61B 5/4362* (2013.01); *A61B 5/4845* (2013.01); *A61B 5/7278* (2013.01)

(58) Field of Classification Search
    CPC ..... A61B 5/349; A61B 5/4362; A61B 5/4845; A61B 5/686; A61B 5/6875; A61B 5/6898; A61B 5/7264; A61B 5/7267; A61B 5/7275; A61B 5/7278; G16H 50/20
    See application file for complete search history.

(56) References Cited

U.S. PATENT DOCUMENTS

| | | | |
|---|---|---|---|
| 5,372,139 | A | 12/1994 | Holls et al. |
| 6,039,701 | A | 3/2000 | Sliwa et al. |
| 6,115,624 | A | 9/2000 | Lewis et al. |
| 6,171,263 | B1 | 1/2001 | Sullivan |
| 6,816,744 | B2 | 11/2004 | Garfield et al. |
| 7,869,863 | B2 | 1/2011 | Moses et al. |
| 8,679,013 | B2 | 3/2014 | Ziarno et al. |
| 8,679,014 | B2 | 3/2014 | Bennett et al. |
| 2002/0193670 | A1 | 12/2002 | Garfield et al. |
| 2005/0267376 | A1* | 12/2005 | Marossero ............ A61B 5/391 600/511 |
| 2006/0084848 | A1 | 4/2006 | Mitchnick |
| 2009/0259133 | A1 | 10/2009 | Wolfberg et al. |
| 2013/0053657 | A1 | 2/2013 | Ziarno et al. |
| 2013/0296735 | A1 | 11/2013 | James et al. |
| 2013/0310704 | A1 | 11/2013 | James et al. |
| 2014/0073879 | A1 | 3/2014 | Cantor et al. |
| 2014/0309943 | A1* | 10/2014 | Grundlehner ........ A61B 5/7264 702/19 |
| 2016/0270670 | A1* | 9/2016 | Oz ........................ A61B 5/30 |

OTHER PUBLICATIONS

Baeten et al., "Use of a vaginal ring containing dapivirine for HIV-1 prevention in women," N. Engl. J. Med., 375(22):2121-2132, Dec. 2016.
Chen et al., "Electronic Fetal Heart Rate Monitoring and Its Relationship to Neonatal and Infant Mortality in the United States," Am. J. Obstet. Gynecol., 204(6):491.e1-10, Jun. 2011.
Clifford, "Blind source separation: principal & independent component analysis," MIT OpenCourseWare, Ch. 15, Spring 2008, 47 pages.
Gonçalves et al., "Toward the improvement in fetal monitoring during labor with the inclusion of maternal HR analysis," MBEC, 54(4):691-699, Apr. 2016.
International Search Report & Written Opinion in International Application No. PCT/US2018/019360 dated May 1, 2018, 11 pages.
Meïgal et al., "EMG characteristics of women in respect with phase of the menstrual cycle, season and type of vegetative regulation," Fiziologiia cheloveka, 40(1):113-21, Jan.-Feb. 2014, (English abstract).
Micussi et al., "Is there a difference in the electromyographic activity of the pelvic floor muscles across the phases of the menstrual cycle?" J. Phys. Ther. Sci., 27(7):2233-2237, Jul. 2015.
who.int [online], "Newborn death and illness, Millennium Development Goal (MDG) 4," Sep. 2011, [retrieved on Feb. 26, 2020], retrieved from: URL<https://www.who.int/pmnch/media/press_materials/fs/fs_newborndealth_illness/en/>.

* cited by examiner

*Convolutional Neural Network System*

Recurrent Neural Network System

SYSTEMS AND METHODS FOR FETAL MONITORING

CROSS-REFERENCE TO RELATED APPLICATIONS

This application is a National Stage application under 35 U.S.C. § 371 of International Application No. PCT/US2018/019360, having an International Filing Date of Feb. 23, 2018, which claims the benefit of U.S. Provisional Ser. No. 62/464,783 filed Feb. 28, 2017. The disclosure of the prior applications are considered part of (and are incorporated by reference in) the disclosure of this application.

BACKGROUND

More than 350,000 babies are born every day, many in developing countries where 45% of infant deaths occur in the neonatal stage. Of 2.6 million stillbirths a year worldwide, 98% occur in developing countries. The United Nations has declared reducing child mortality as one of its millennium goals and in its 2016 fact sheet states: "Up to two thirds of newborn deaths could be prevented if skilled health workers perform effective health measures at birth and during the first week of life . . . " Research has shown a strong connection between intrapartum still birth, neonatal death, infant morbidity and lack of fetal heart monitoring in the United States and in developing nations. In the United States, fetal heart monitoring has been widely adopted and is used in 86% of deliveries. Typical fetal heart-rate monitoring uses ultrasound technology and can require considerable expertise for use. For example, motion can result in artifacts, signal dropout, and inadvertent acquisition of the maternal rather than fetal heart rate.

SUMMARY

This specification describes systems, methods, devices, and other techniques for fetal monitoring.

Some aspects of the disclosed subject matter include a vaginal probe for sensing information about a patient from within a vaginal canal. The probe may include a ring-shaped body, one or more sets of sensors, a wireless communications interface, a wired communications interface, and a controller. Shapes and form factors other than a "ring" may also be implemented, such as a tampon, cylinder, or a cup-shaped device, any of which can include a multi-sensor array. By way of example, this specification sometimes refers to a ring-shaped probe, but it should be understood that other form factors may also be suitable. In some implementations, the set of sensors includes a set of ECG sensors that include one or more electrodes disposed on the ring-shaped body and configured to capture an ECG signal that at least partially represents fetal cardiac activity. The wireless communications interface is configured to wirelessly transmit radio frequency (RF) signals that encode information about a maternal ECG signal or a mixed maternal-fetal ECG signal. The controller can be configured to activate or deactivate signal acquisition from the one or more sets of sensors and to control wireless transmission of data from the probe.

Other aspects of the disclosed subject matter include a computer-implemented method. The method can include obtaining, by a system of one or more computers, a maternal electrocardiogram (ECG) signal that represents an ECG of a pregnant mother during a first time interval; obtaining, by the system, a mixed maternal-fetal ECG signal that represents a combined ECG of the mother and her fetus during the first time interval; processing, by the system, the maternal ECG signal and the mixed maternal-fetal ECG signal to generate a fetal ECG signal that represents the ECG of the fetus during the time interval, the fetal ECG signal substantially excluding the maternal ECG signal; and providing, by the system, an output based on the fetal ECG signal.

Yet other aspects of the disclosed subject matter include a computer-implemented method that includes receiving, by a system of one or more computers, a first ECG signal, wherein the first ECG signal is (i) a mixed maternal-fetal ECG signal that represents a combined ECG of a pregnant mother and her fetus or (ii) a fetal ECG signal that represents an ECG of the fetus substantially to the exclusion of an ECG of the mother; processing, by the system, the first ECG signal to determine values for one or more features of the first ECG signal; determining, based on the determined values for the one or more features of the first ECG signal, a condition of at least one of the mother or the fetus; and providing, by the system, an output based on the determined condition of the at least one of the mother or the fetus.

In some implementations, a system is configured to monitor and analyze a fetal heart rate pattern (e.g., decreases in heart rate or other changes) to identify/screen for a substance-dependent mother (e.g., a mother who has consumed opioids), thereby allowing early intervention to prevent or mitigate occurrences of neonatal abstinence syndrome. In another aspect, the invention described herein can identify/screen for alcohol dependent mothers so early intervention can be implemented to prevent or mitigate Fetal Alcohol Syndrome.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other reference mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

The details of one or more implementations are set forth in the accompanying drawings and the description below. Other features, objects, and advantages will be apparent from the description and drawings, and from the claims.

DETAILED DESCRIPTION

This specification describes systems, methods, devices, and other techniques for performing fetal monitoring. In some aspects, a ring-shaped vaginal probe includes embedded electrodes to enable preferential acquisition of fetal ECG signals as a result of its close proximity to the fetus when inserted in the mother's vaginal canal. In some aspects, computer-based processing techniques using vector signal processing and independent component analysis, coupled with the ring-shaped vaginal probe, may facilitate robust, continuous, fetal HR monitoring and analysis.

Conventionally, fetal monitors have relied upon skin-surface Doppler and ultrasound technology to detect and record a fetus's heart rate over time. A fetal ECG (e.g., a tracing of the electrical activity of the fetus's heart) is typically only available using scalp electrodes affixed to the fetus's head after membrane rupture, and even this option will usually be unavailable when the fetus is in a breach presentation. Accordingly, the techniques described herein are intended to at least partially overcome these shortcomings of conventional fetal monitoring. For example, simultaneous maternal and fetal ECG monitoring may permit early detection of fetal academia, potentially preventing cerebral palsy caused by hypoxemia at birth. Additionally, the ring-shaped vaginal probe may permit acquisition of additional biomarkers such as an electromyogram (EMG), temperature, and intra-vaginal fluid characteristics. In some implementations, the ring-shaped vaginal probe may facilitate home-based fetal monitoring for sustained periods of time (e.g., continuous monitoring). In some implementations, the vaginal probe may be used for pregnancy planning purposes. For example, temperature sensors, EMG electrodes, or both, may be used to monitor changes in conditions of the pubic region of a woman over time during a menstruation cycle. The woman may use such information to plan intercourse for appropriate times, e.g., to either avoid pregnancy or to increase the likelihood of conception.

Figure 1:
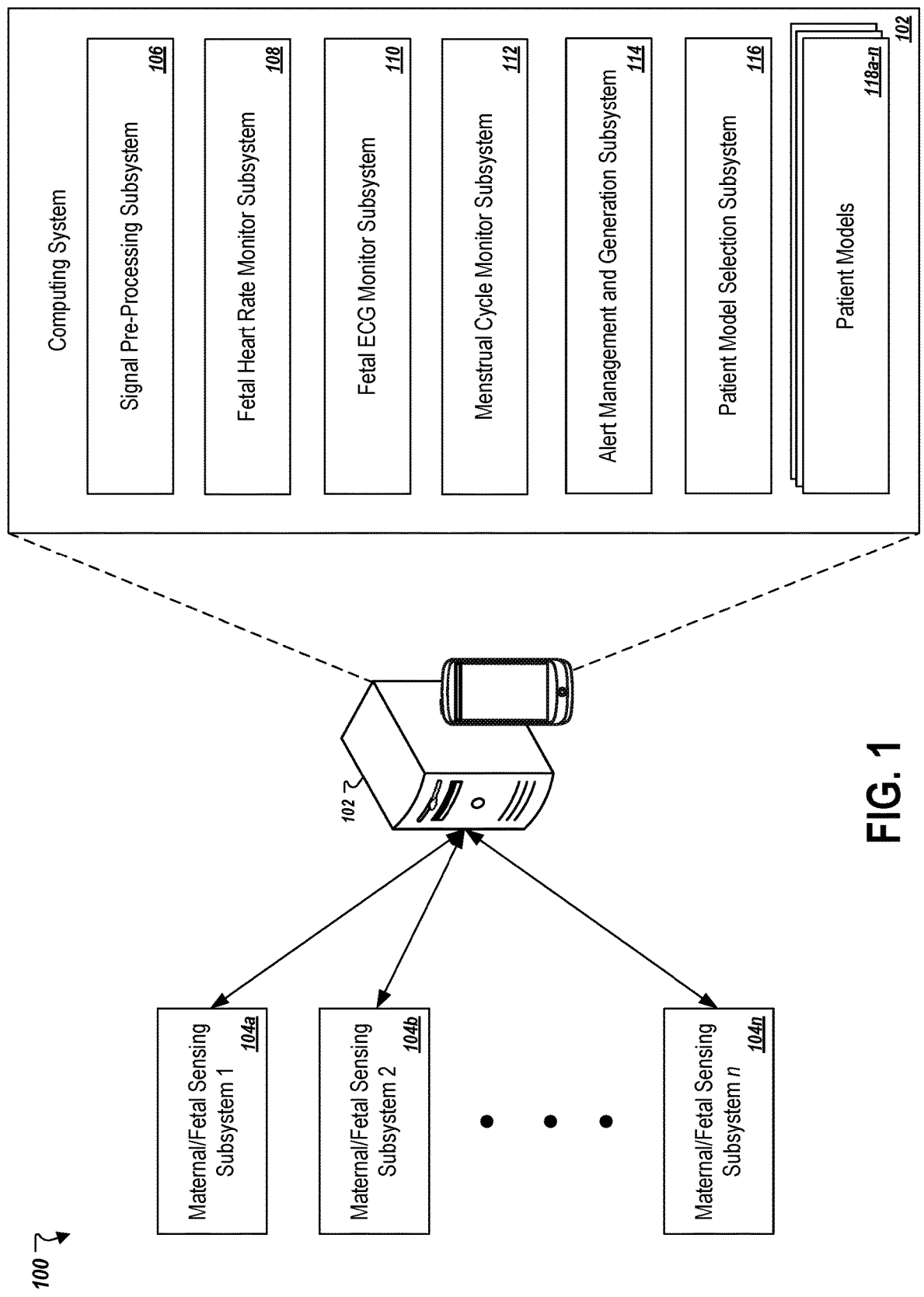
FIG. 1 is an illustration of an example environment for fetal monitoring.

Referring to FIG. 1, an example environment 100 for fetal monitoring is depicted. The environment 100 includes a system 102, where the system 102 includes one or more computers in one or more locations. The system 102 includes one, two, three, or more data acquisition channels for obtaining sensor data representing signals detected by sets of sensors 104*a-n* coupled to a patient. In general, the patient will be described herein as a pregnant mother, although in other instances the patient may not be pregnant, e.g., a woman who is tracking her menstrual cycle to increase or decrease the likelihood of becoming pregnant as a result of intercourse. Each data acquisition channel of the system 102 obtains data from a different set of sensors 104*a-n*. For example, a first set of sensors 104*a* may be ECG sensors (e.g., electrodes) located on a chest or abdominal region of the patient, e.g., skin-surface ECG sensors such as in an abdominal patch. A second set of sensors 104*b* may be ECG sensors (e.g., electrodes) located on an inserted vaginal probe located nearer the fetus. The system 102 may obtain ECG signals from each set of sensors 104*a*, 104*b*, and may process both to determine a fetal ECG signal. The system 102 can be configured to extract a fetal ECG signal from a mixed maternal-fetal ECG signal, and optionally, from a maternal ECG signal that substantially excludes the fetal ECG signal. In some implementations, the system 102 processes a mixed maternal-fetal ECG signal obtained from vaginal ECG sensors alone (e.g., without signals from abdominal or other skin-surface ECG sensors). In some implementations, the system 102 processes a mixed maternal-fetal ECG signal obtained from abdominal or other skin-surface ECG sensors alone (e.g., without signals from vaginal ECG sensors). In some implementations, the system 102 processes a mixed maternal-fetal ECG signal obtained from both vaginal ECG sensors and abdominal or other skin-surface ECG sensors (e.g., using electrode(s) placed on the patient's thigh as a reference). The latter, hybrid, approach may be useful in some instances where a reference electrode is available. A wire to an extra-vaginal electrode may serve as an antenna for external communication.

The system 102 may include all or some of components 106-118. Each component 106-118 may include a combination of software and hardware that are configured to perform the operations described herein.

The signal pre-processing subsystem 106 receives sensor data from the sets of sensors 104*a-n*. If the received sensor data is in analog form, the subsystem 106 may use an analog-to-digital converter to sample and digitize the sensor signals. The pre-processing subsystem 106 may also amplify and filter all or some of the signals from the sensors 104*a-n* to prepare the signals for further processing. In some implementations, the pre-processing subsystem 106 synchronizes signals from different sets of sensors 104*a-n*. For instance, two channels of ECG sensor data may be synchronized so that the beats shown in waveforms among each of the channels are aligned in the time dimension. In some instances, synchronization is performed by using a common clock or synchronized clocks to timestamp frames of data from each sensor data that are received concurrently on each channel.

The fetal heart rate monitor subsystem 108 is configured to process at least one of a fetal ECG signal or a mixed maternal-fetal ECG signal to determine the heart rate of a fetus. The heart rate may be an instantaneous or average heart rate over a window of time. In some implementations, as described with respect to FIGS. 7, 8, and 10 below, the fetal heart rate monitor subsystem 108 uses a neural network system, e.g., including one or more convolutional or recurrent neural networks, to process the input ECG signal to determine the fetal heart rate. Other machine-learning or predictive models may also be employed to process input ECG signal(s) and to determine the fetal heart rate, such as computation of invariants such as multiscale contractions, linearization of hierarchical symmetries, sparse separations, unsupervised clustering, or a combination of these and other techniques.

The fetal ECG monitor subsystem 110 is configured to determine a fetal ECG signal from one or more input ECG signals. The input ECG signals can include a mixed maternal-fetal ECG signal and, optionally, a maternal ECG signal that is substantially independent of the fetal ECG signal. The mixed maternal-fetal ECG signal may be obtained, for example, from a ring-shaped vaginal probe having ECG electrodes therein that is inserted in the vaginal canal of the mother. Due to the close proximity to the fetus, the influence of the fetal ECG may be more pronounced on the signal detected by the vaginal probe than if the ECG signal were acquired by sensors affixed to the patient at other locations, such as an abdominal patch through use of a standard 12-lead ECG. The signal detected by the electrodes on the vaginal probe may also be significantly influenced by the mother's own cardiac electrical activity. Thus, the signal detected by the vaginal probe may be a mix of both the maternal ECG signal and the fetal ECG signal.

In some implementations the fetal ECG monitor subsystem 110 includes a fetal ECG analysis engine. The fetal ECG analysis engine processes a fetal ECG signal and predicts likelihoods that the mother or fetus has, or is at risk of developing, one or more conditions based on features of the fetal ECG signal. For example, the fetal ECG analysis engine may determine a representative fetal beat waveform from the fetal ECG signal by excluding noisy beats from a set of beats over a timer interval and averaging or otherwise combining the non-excluded beats. Alternatively, the representative fetal beat may be selected from the set of beats based on one or more criteria. The fetal ECG monitor subsystem 110 determines values for one or more features of the beats. Examples of features of the representative beat are features of its waveform such as Q-T intervals, slope of the ascending portion of the T-wave, slope of the descending portion of the T-wave, maximum or average amplitude of the T-wave, area under the T-wave, or corresponding features for other portions of the waveform such as the QRS complex. The feature values can then be provided as input to a model, e.g., a statistical model, a rules-based model, or an artificial neural network, to generate scores that represent the likelihoods of one or more maternal or fetal conditions occurring such as fetal academia, fetal $pO_2$, fetal pH, and/or fetal cardiac anomalies. The patient or a healthcare provider may be alerted if the likelihoods of certain conditions are sufficiently high. Other machine-learning or predictive models may also be suitable, such as computation of invariants such as multiscale contractions, linearization of hierarchical symmetries, sparse separations, unsupervised clustering, or a combination of these and other techniques.

The menstrual cycle monitor subsystem 112 is configured to provide services related to menstrual cycle tracking for a woman. The subsystem 112 obtains data from one or more sources including data representing a high fidelity electromyogram (EMG) signal detected by EMG sensors/electrodes an inserted vaginal probe. The EMG sensors may be configured to contact the cervix in use to obtain high fidelity signals. In some implementations, the subsystem 112 also obtains and processes temperature signals sensed by one or more temperature sensors on the vaginal probe. Using the sensor data representing EMG signals, temperature signals, or both, the menstrual cycle monitor subsystem 112 uses a personalized menstrual cycle model to precisely identify the timing of when ovulation has occurred. The model may further be applied to predict ovulation timing. Accordingly, the patient may be able to reduce or increase the probability of conceiving as a result of intercourse.

The alert management and generation subsystem 114 is configured to generate and present alerts to one or more users when a defined alert event is detected to have occurred, or is predicted to occur. For example, the alert subsystem 114 may continuously monitor a fetal heart rate and distress level. If the heart rate or distress level becomes too high and exceeds a threshold heart rate or distress level (e.g., exceeds once, multiple times, or for a minimum period of time), then an alert may be generated. Alerts may be in any suitable form to grab users' attention such as audible, visual, or haptic feedback, or a combination of these. In some implementations, the alert subsystem 114 generates a message for a user in an external communication channel such as email, SMS messages, mobile alerts, or social media alerts. In some implementations, the vaginal probe may include a vibration mechanism such as an off-balanced motor that provides vibratory feedback to the patient when the probe is inserted in the vaginal canal in response to detecting certain events. For example, vaginal probe may be configured to vibrate if the fetal heart rate or distress level exceeds a threshold. For menstrual cycle monitoring, the vaginal probe may vibrate to alert the woman to phases of the cycle, such as the beginning or end of fertility windows. Vibratory alerts can be beneficial to generate brief vibration pulses in a private manner without the need for the patient to read alerts from an external device.

In some implementations, the system 102 further includes a set of global or personalized patient models 118a-n. The patient models 118a-n may be used by the fetal heart rate monitor subsystem 108, the fetal ECG monitor subsystem 110, or both to determine heart rate, distress levels, fetal ECG, or other outputs based on one or more input signals such as a maternal ECG signal and a mixed maternal-fetal ECG signal. In some implementations, the patient models 118a-n are binned based on characteristics of the mother, fetus, or both. For example, the system 102 may select a different one of the models 118a-n depending on the age and weight of the mother and based on the gestational age of the fetus.

Figure 2:
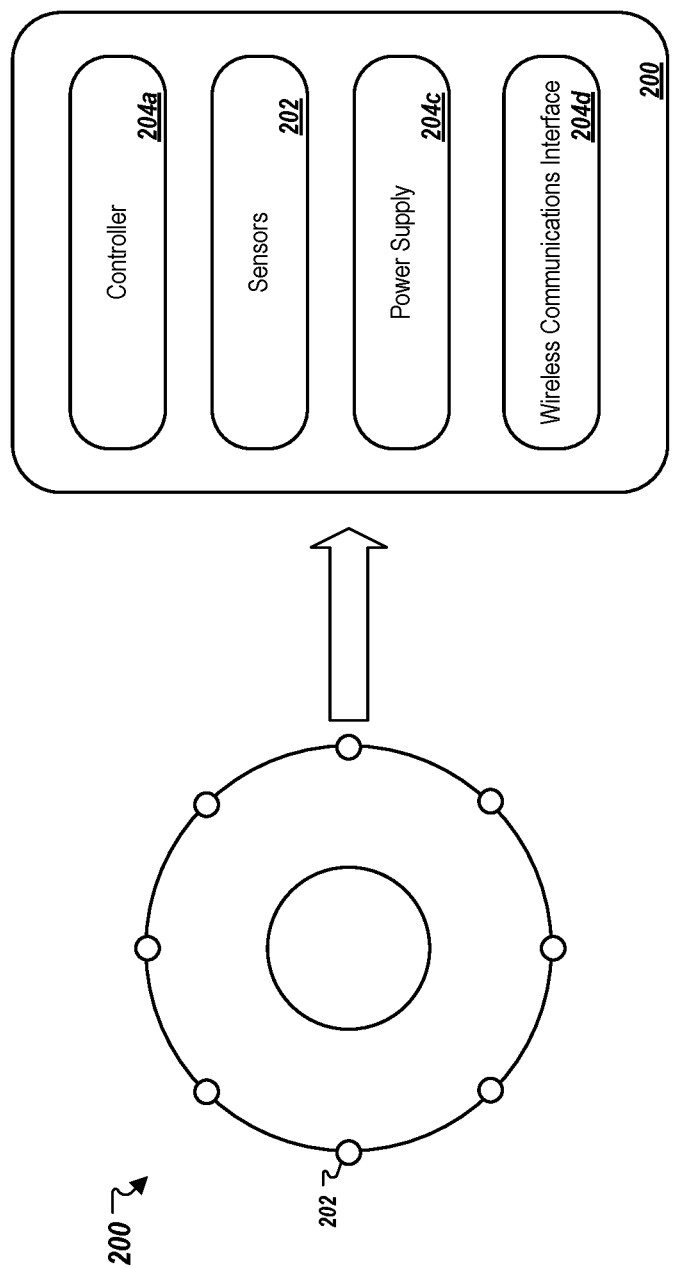
FIG. 2 is a diagram of an example vaginal probe.

FIG. 2 is a diagram of an example vaginal probe 200. The vaginal probe 200 is configured to be inserted within the vaginal canal of a patient to permit monitoring of one or more conditions related to the reproductive areas of the patient and/or of a fetus of a pregnant patient. In some implementations, the vaginal probe is an independent, optionally flexible, device that can be readily inserted by a patient (self-insertable) that records physiologic information about the patient and wirelessly transmits the physiologic information to an external device such as a smartphone or dedicated reader. Although in some implementations the vaginal probe may additionally or alternatively contain a wire "tail" that physically connects the probe in use to an external device, in other implementations the vaginal probe is independent and relies on wireless RF transmissions to communicate with an external device.

Figure 3:
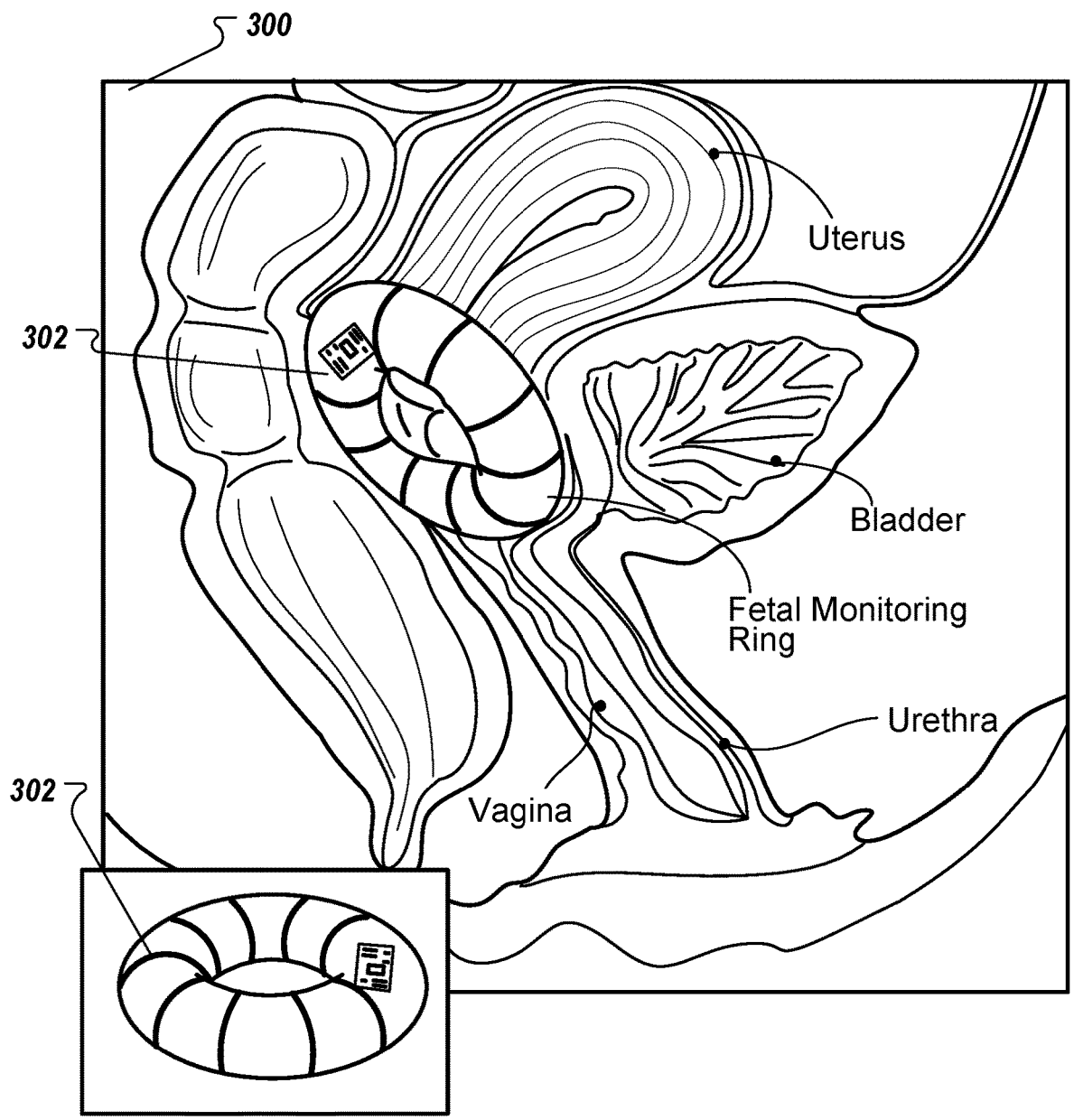
FIG. 3 is an illustration of an example placement of a vaginal probe in the vaginal canal of a patient.

The vaginal probe 200 can include a collection of sensors 202 that are configured to produce signals indicating one or more conditions of the patient (e.g., physiologic information) that are detectable from the vaginal canal. The sensors 202 can include one or more of ECG sensors/electrodes, EMG sensors/electrodes, pH sensors, ultrasound sensors, ultrasound transmitter, temperature sensors, and sensors that are configured to detect the presence of specific chemicals or fluids. The body of the probe may have a ring-like shape, e.g., made from a metallic alloy such as nitinol, that is structured and dimensioned to be inserted within the vaginal canal as depicted in FIG. 3, which shows an example vaginal ring (probe) 302 inserted within the vaginal canal of a patient to allow for monitoring of various conditions from within the canal. In some implementations, the vaginal probe may have a shape or form factor other than a "ring," such as a tampon, cylinder, or a cup-shaped device with multi-sensor array. By way of example, this specification generally refers to a ring-shaped probe, but it should be understood that other shapes or form factors may be suitable as well. The rings 200, 302 can include a controller 204a, one or more sets of sensors 202, a power source 204c, and a wireless communications interface 204d. The wireless communications interface 204d is configured to transmit RF signals encoded with information characterizing sensor data to an external computing system, e.g., system 102. In some implementations, the external computing system is or includes a smartphone, a wearable device, a tablet, or another mobile device that allows the patient or the patient's healthcare provider to easily receive data wirelessly transmitted from the vaginal probe. In some implementations, the wireless interface 204d is a BLUETOOTH® radio including a short-range radio transmitter and receiver, or is an IEEE 802.11 WI-FI radio. The controller 204a can be a microcontroller or other data processing apparatus configured to control, for example, parameters for how and when data from one or more of the sets of sensors 202 is captured and transmitted to the external computing system.

The vaginal probe 200 can include a power supply 204c, which may either be an active power source such as a rechargeable battery, or a passive power source. For implementations that provide a passive power source, the probe 200 may include one or more metallic coils that are configured to generate electrical power based on induction from an inductive power source external to the patient that is brought in proximity (e.g., less than about 2 inches, less than about 1 inch, less than about 0.5 inches, or less than about 0.25 inches) of the coil in the vaginal probe 200. In some implementations, the controller 204a of the probe 200 is configured to only activate signal acquisition/capture from the sensors 202 and/or to cause the wireless interface 204d to transmit sensor data only when the external, inductive power source is brought into proximity of the probe 200 when the probe 200 is located in the vaginal canal of the patient.

Figure 9:
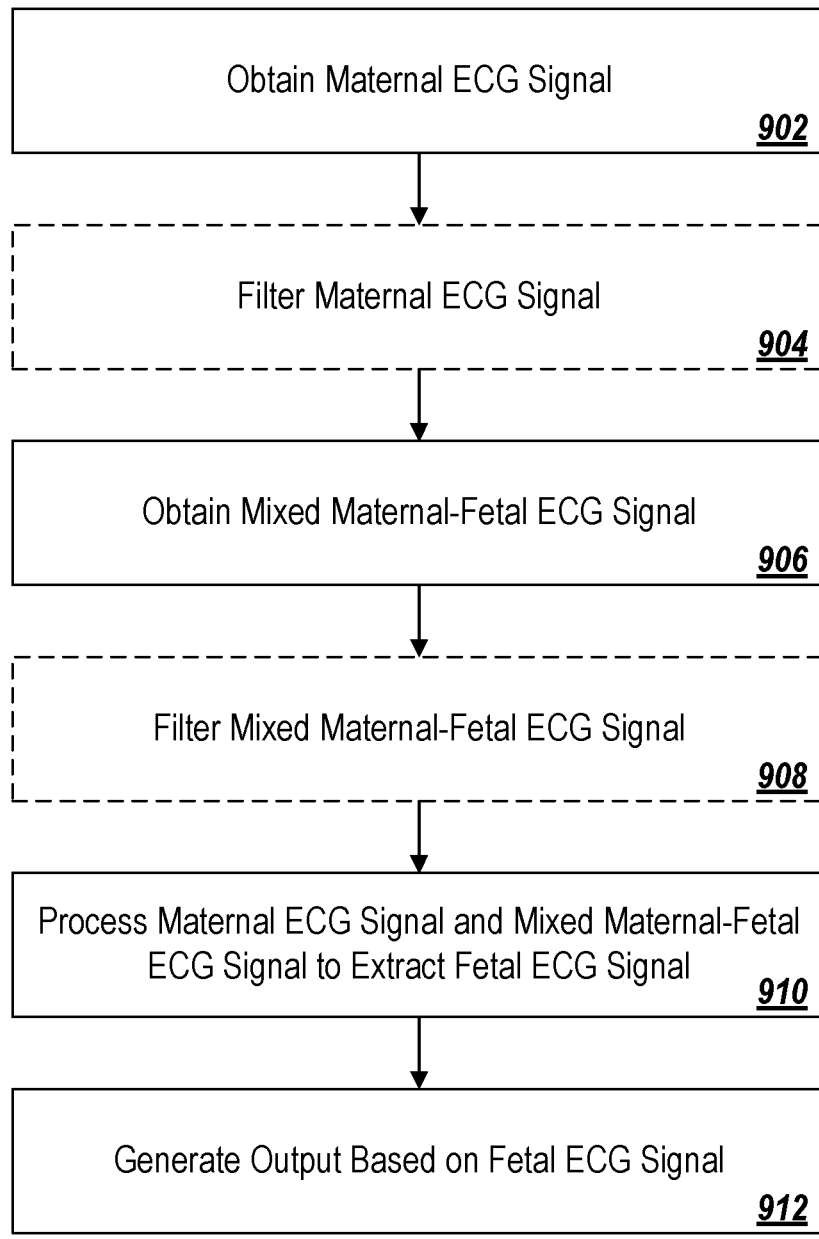
FIG. 9 depicts a flowchart for an example process for generating a fetal ECG signal from a maternal ECG signal and a mixed maternal-fetal ECG signal.

In some implementations, a computing system can obtain sensor data from which a fetal ECG signal is determined. FIG. 9 depicts a flowchart for an example process 900 for generating a fetal ECG signal from a maternal ECG signal and a mixed maternal-fetal ECG signal. The process 900 may be carried out, for example, by a fetal ECG monitor of a computing system, e.g., fetal ECG monitor subsystem 110 of system 102. At stage 902, the system obtains a maternal ECG signal that represents electrical activity of the heart of a pregnant mother. The ECG signal may show a repetitive waveform, for example, in an electrical tracing that indicates the electrical potential between particular lead vectors coupled to the patient. The maternal ECG signal may be obtained, for example, from an abdominal or chest region of the patient and may be sufficiently distant from the fetus such that any influence of the fetal ECG may be de minimis. Optionally, at stage 904, the maternal ECG signal may be filtered, e.g., using a Wiener filter.

At stage 906, the system obtains a mixed maternal-fetal ECG signal. The mixed maternal-fetal ECG signal may be obtained, for example, from a vaginal probe, e.g., probe 200, from within a vaginal canal of the mother. The ECG electrodes on the probe 200 may be positioned near the uterus or other organ to be as close as feasible to the fetus in order to permit capturing of signals resulting from the fetal heartbeat. Because the electrodes are still not directly coupled to the fetus, the captures ECG signal is a mixed maternal-fetal ECG signal. In some implementations, the power contribution of the maternal ECG signal may be much greater than the power contribution of the fetal ECG signal. At stage 908, the mixed maternal-fetal ECG signal is optionally filtered by one or more digital filters.

At stage 910, the system processes the maternal ECG signal and the mixed maternal-fetal ECG signal to isolate the fetal ECG signal. In some implementations, the fetal ECG signal is obtained by subtracting the maternal ECG signal from the mixed maternal-ECG signal. In some implementations, blind source separation, independent component analysis (ICA), principal component analysis (PCA), or a combination of these can be performed to separate the fetal ECG signal using the pair of input signals, i.e., using the maternal ECG signal and the mixed maternal-fetal ECG signal. Furthermore, in some implementations, the system may select a particular ECG vector for the maternal-fetal ECG and/or for the maternal ECG signal in order to optimize the ability to extract a high fidelity fetal ECG signal. An ECG vector refers to the ECG signal that results from the electrical potential between a particular pair of ECG leads/sensors. For example, a ring-shaped vaginal probe may have 2, 4, 6, 8, 10, or 12 ECG leads in some implementations. The electrical potential as measured between each possible pair of leads constitutes an ECG vector. The system may select a particular pair of leads and corresponding ECG vector to process in determining a fetal ECG signal based on various criteria such as signal to noise ratio, positioning of the leads in the vaginal canal, spacing of the leads on the probe, or a combination of these. For example, if the vaginal probe rotates to some degree in use, or if the position of the fetus changes relative to the location of the probe, the system may dynamically re-select leads and corresponding ECG vectors to obtain an optimal fetal ECG as conditions change.

Figure 5:
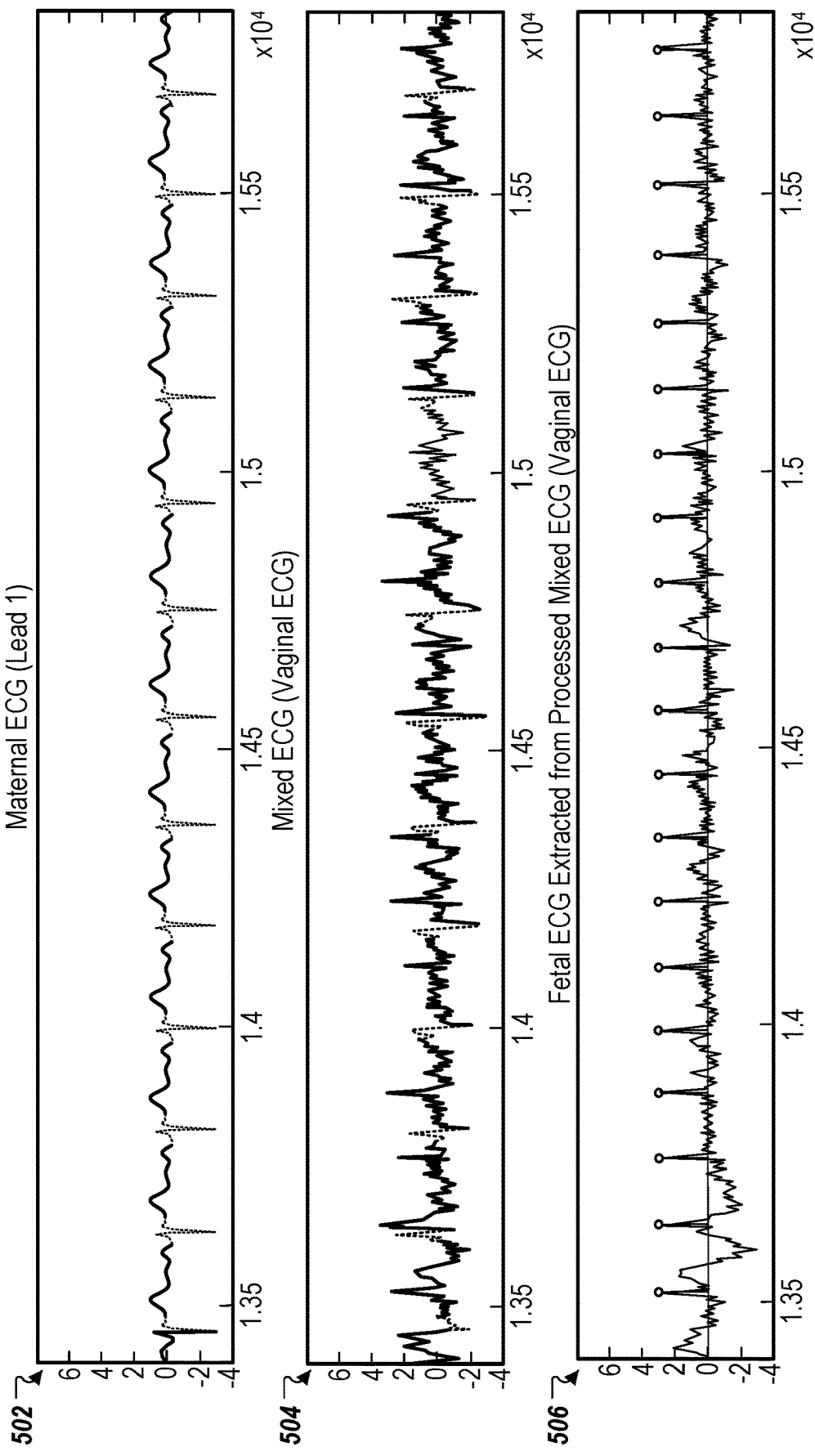
FIG. 5 depicts a set of ECG waveforms plotted over a common time interval.

At stage 912, the system generates an output using the fetal ECG signal. For example, a tracing of the fetal ECG waveform may be displayed on a monitor for presentation to the patient or healthcare provider. FIG. 5 depicts a set of ECG waveforms plotted over a window of time. A maternal ECG signal is represented by plot 502, a mixed maternal-fetal ECG signal is represented by plot 504, and a fetal ECG signal that has been extracted from the mixed maternal-fetal ECG signal is represented by plot 506.

Figure 4:
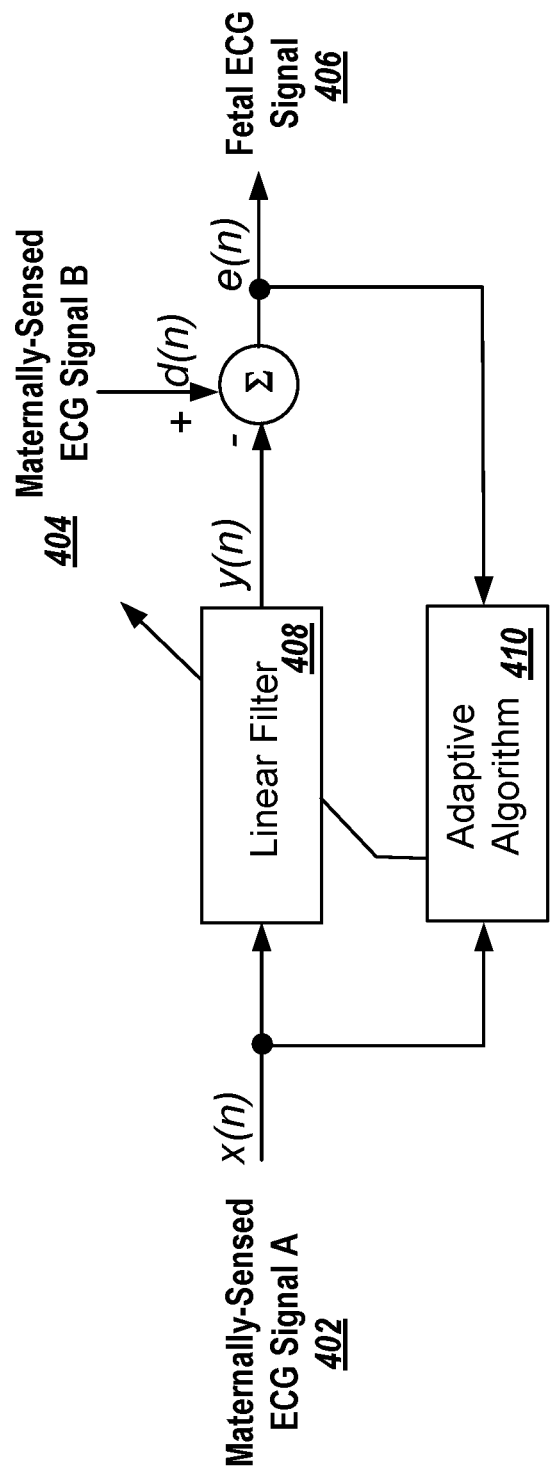
FIG. 4 depicts an example feedback filtering system that is configured to process a maternal ECG signal and a mixed maternal-fetal ECG signal to extract a fetal ECG signal.

FIG. 4 shows a feedback filtering system for extracting a fetal ECG signal. The system provides a maternal ECG signal 402 to a filter 408, which outputs a filtered maternal ECG signal. The filtered maternal ECG signal is then subtracted from a mixed maternal-fetal ECG signal 404 to recover the fetal ECG signal 406. In some implementations, the fetal ECG signal 406 is used as feedback to an adaptive component of the filter 408 to adjust parameters of the filter 408 based according to current conditions of the fetal ECG signal 406.

Figure 6:
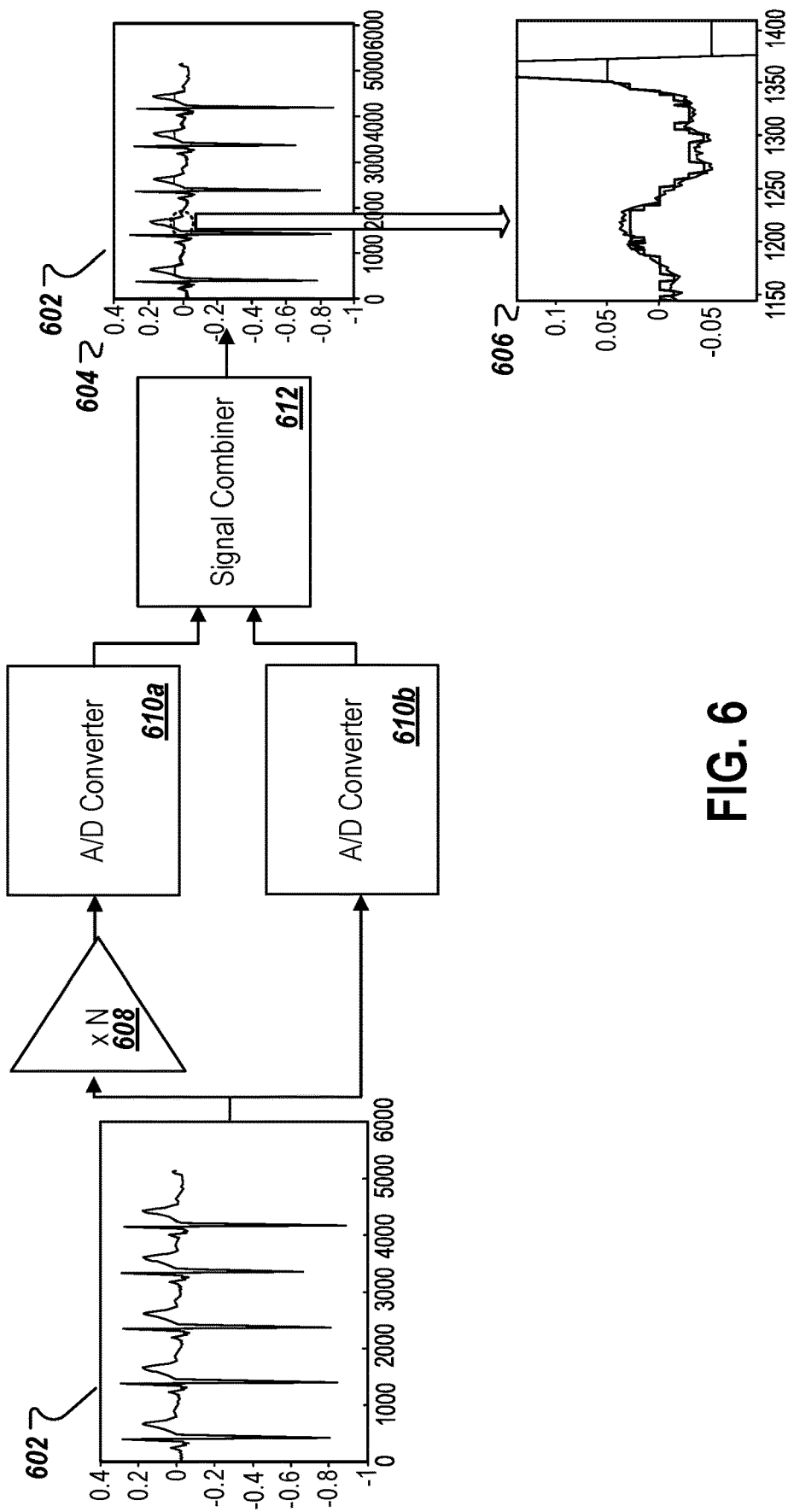
FIG. 6 is a schematic illustration of a dual-sampling technique that a system may employ on a mixed maternal-ECG signal to optimize the signal for further processing.

FIG. 6 is a schematic illustration of a dual-sampling technique that a system may employ on a mixed maternal-ECG signal to optimize the signal for further processing. A mixed maternal-ECG signal 602 is sampled twice, i.e., once by A/D converter 610a and once by A/D converter 610b. The first A/D converter 610a samples the signal 602 after it has been amplified by amplifier 608. The amplified signal may extend outside the dynamic range of the A/D converter 610a, thereby causing peaks in the maternal ECG portion of the signal to be clipped. The signal combiner 612 combines the signals from each A/D converter 610a, 610b to generate a higher resolution signal that what may otherwise have been sampled.

Figure 7:
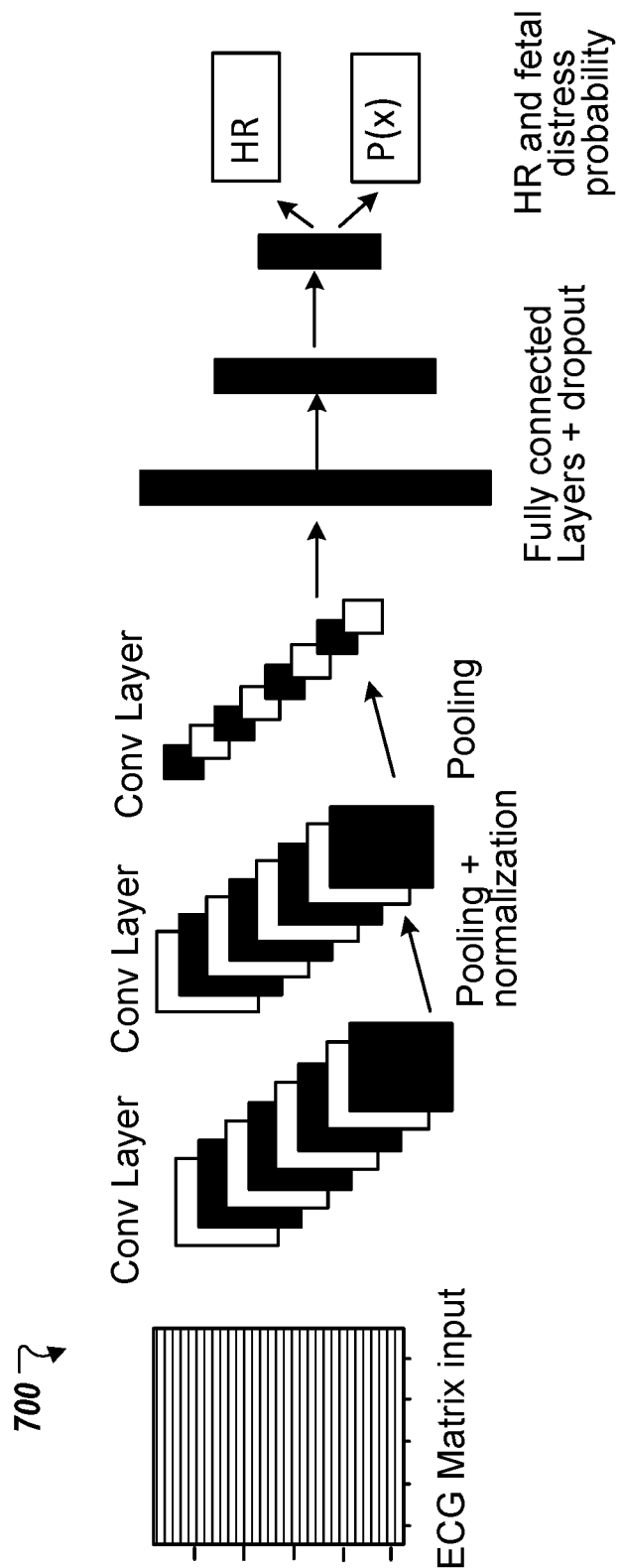
FIG. 7 is a schematic illustration of an example convolutional neural network system configured to estimate a heart rate and distress level of a fetus based on ECG signals.
Figure 8:
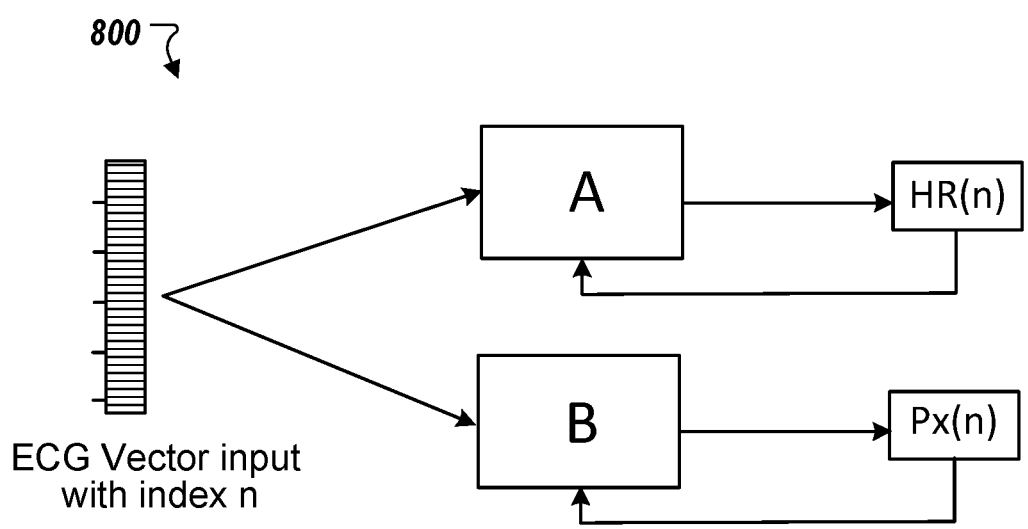
FIG. 8 is a schematic illustration of an example recurrent neural network system configured to estimate a heart rate and distress level of a fetus based on ECG signals.

FIGS. 7 and 8 depict illustrate example neural network systems that are trained to generate outputs representing a fetal heart rate based on an input ECG signal and, optionally, auxiliary patient data. The input ECG signal can be, for example, the fetal ECG signal or the mixed maternal-fetal ECG signal. In some implementations, the neural network system is a convolutional neural network. FIG. 7 depicts an example convolutional neural network 700. In other implementations, the neural network system is a recurrent neural network. FIG. 8 depicts an example recurrent neural network 800.

Neural networks are machine learning models that employ one or more layers of nonlinear units to predict an output for a received input. Some neural networks include one or more hidden layers in addition to an output layer. The output of each hidden layer is used as input to the next layer in the network, i.e., the next hidden layer or the output layer. Each layer of the network generates an output from a received input in accordance with current values of a respective set of parameters.

The neural networks may be global models or personalized model. For global models, the network can be trained using a retrospective database of maternal and fetal ECG with fetal hear rate as the target output, where the fetal heart rate in the training data may have been ascertained in any suitable manner (e.g., directly using scalp electrodes, CTG device). The model may also use auxiliary patient data at training stage, such as the baby's pH level (e.g., a marker for acidimia), electrolytes from umbilical cord blood, oxygen level, cardiac anomalies, and others to predict fetal distress using the input ECG signal. The global model can be a single model or multiple models based on bins such as mother's weight, age, maternal heart rate in rest, or a combination of these and other factors. For personalized models, after positioning the ECG sensors on the mother, a training session is performed to train the model specifically to the particular mother.

The recurrent neural network can be configured to continuously process neural network inputs representing the input ECG signal for a respective period of time. The convolutional neural network can be configured to receive portions of the input ECG signal, where the windows represented by each portion may overlap. For both the recurrent and convolutional network implementations, the neural network system outputs information indicating the fetal heart rate (e.g., 30-200 bpm) and the likelihood (e.g., probability) for fetal distress. In some implementations, the thresholds for determining when to generate an alert may be based on both the fetal hear rate and predicted fetal distress.

Figure 10:
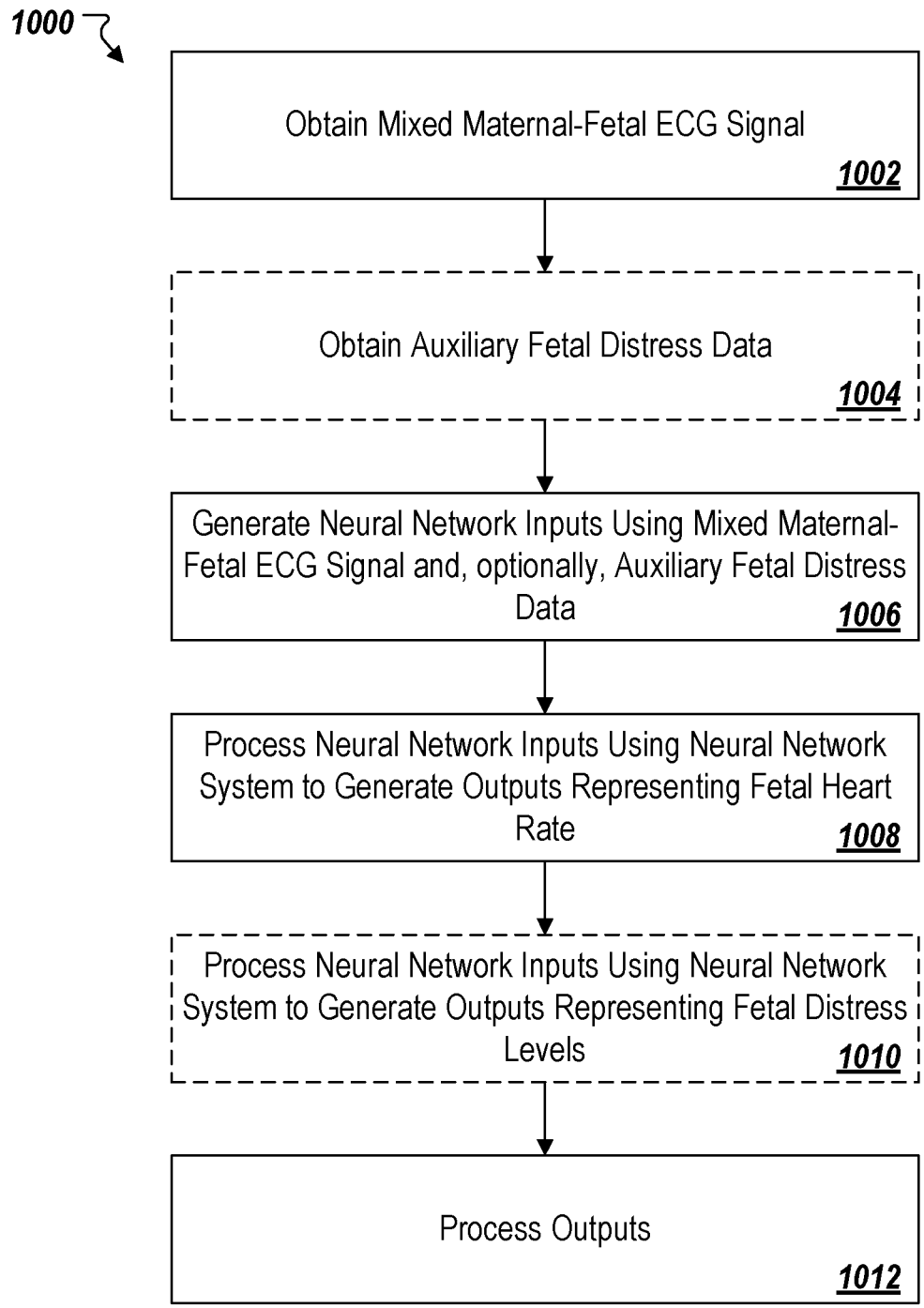
FIG. 10 depicts a flowchart of an example process for processing an input ECG signal of a mother to generate outputs representing fetal heart rate, fetal distress level, or both.

FIG. 10 depicts a flowchart of an example process 1000 for processing an input ECG signal of a mother to generate outputs representing fetal heart rate, fetal distress level, or both. In some implementations the process 1000 is performed using a neural network system such as the recurrent or convolutional neural network systems depicted in FIGS. 8 and 9. The neural network system first obtains an input ECG signal, e.g., a mixed maternal-fetal ECG signal (1002). Optionally, the system also obtains auxiliary fetal distress data (auxiliary patient data) (1004). The system generates neural network inputs based on the mixed maternal-fetal ECG signal and, optionally, auxiliary fetal distress data (1006). The neural network then processes the neural network inputs to generate outputs representing fetal heart rate, and optionally, an indication of a fetal distress level (1008 and 1010). Having determined the heart rate and fetal distress level, the system may then process these outputs in any suitable manner. In some implementations, the system generates an alert to notify a user of the occurrence of a detected problem or other pre-defined event, e.g., if the heart rate and fetal distress level are outside acceptable boundaries as indicated by one or more threshold values.

Figure 11:
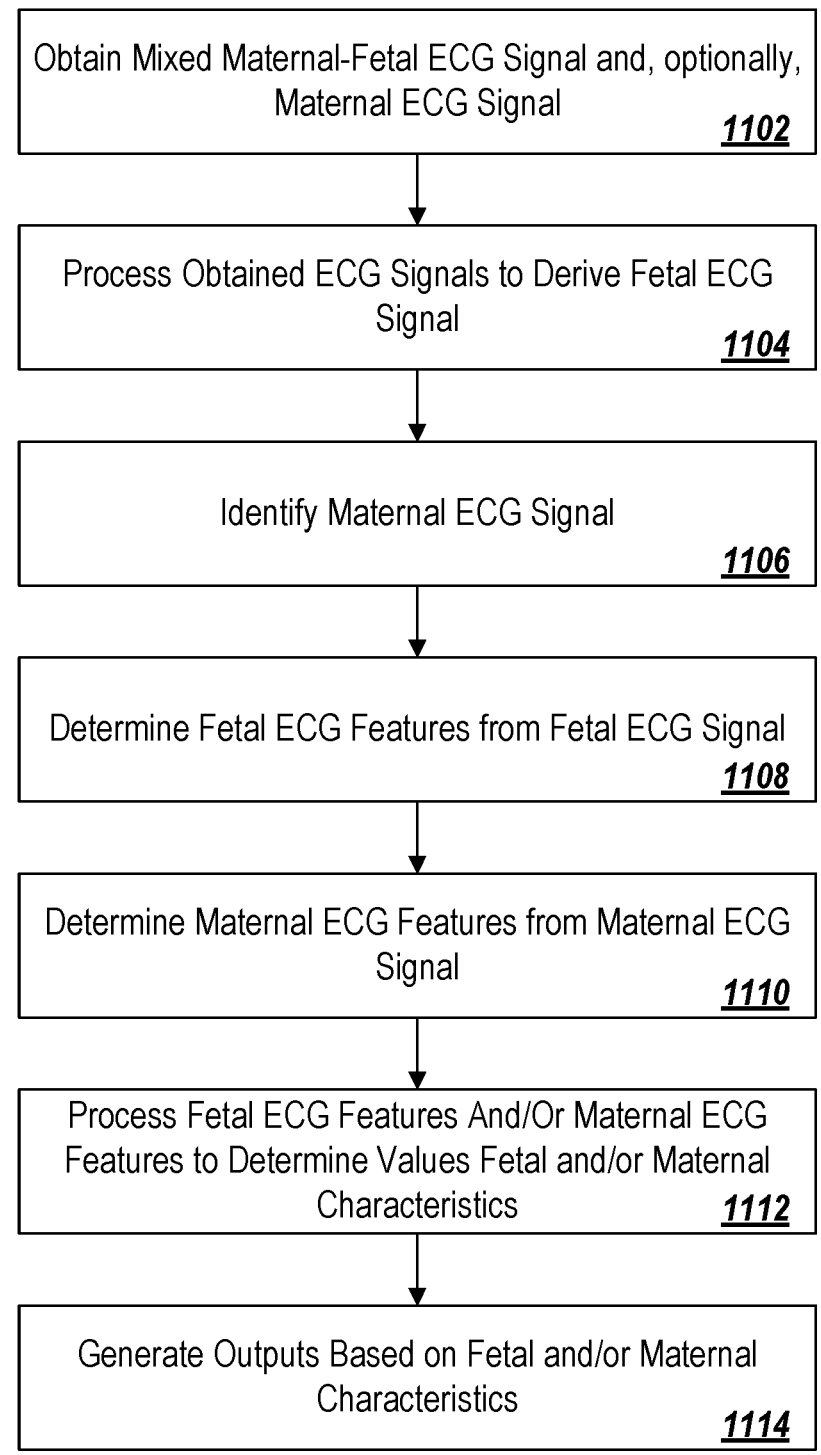
FIG. 11 depicts a flowchart of an example process for extracting and processing fetal ECG signals.

FIG. 11 depicts a flowchart of an example process 1100 for extracting and processing fetal ECG signals. In some implementations, the process is carried out by a system of one or more computers, e.g., system 102. At stage 1102, the system obtains a mixed maternal-fetal ECG signal and, optionally, a maternal ECG signal. At stage 1104, the system processes the obtained ECG signal to derive a fetal ECG signal (stage 1104). At stage 1106, the system identifies the maternal ECG signal that corresponds to the mixed signal for processing. At stage 1108, the system analyzes the fetal ECG signal to determine features of a representative beat in the fetal ECG signal. At stage 1110, the system analyzes the maternal ECG signal to determine features of a representative beat the maternal ECG signal. At stage 1112, the system processes fetal ECG features and/or maternal ECG features to determine values indicative of one or more maternal and/or fetal conditions. At stage 1114, the system generates alerts, reports, or other outputs based on determined values that indicate likelihoods of one or more maternal and/or fetal conditions.

In some implementations, the systems described herein may be adapted to additional or alternative aspects, including, for example, a system for detecting physiologic changes in an infant or otherwise young individual (e.g., under 3, 6, 9, 12, 15, 18, 21, 24, or 36 months of age) is contemplated, especially where the detected changes relate to symptoms of neonatal abstinence syndrome. The system may thus be utilized as a screening tool for the syndrome. Neonatal abstinence syndrome generally refers to the withdrawal experienced by infants after birth, although in this case it can also refer to the experience of fetuses in utero due to the withdrawal of drugs of dependence from when they are abused antenatally by the mother. The physiologic changes in association with drug withdrawal depends on the specific drug withdrawn, but can include changes in heart rate, respiratory rate, agitation, gastrointestinal changes, convulsions, high-pitched cry, Moro reflex, tremors, irritability, altered sleep, or a combination of these. Elevated temperature, tachypnea, apnea, nasal congestion, nasal flaring, and yawning have also been described. According to the techniques here, the system can include one or more sensors configured to be worn or embedded in a shirt, and that by means of artificial intelligence or other models (e.g., machine-learning models such as deep neural networks), can identify the physiologic changes to suggest withdrawal from such substances. For example, the system may monitor, via data obtained from the sensors, changes in maternal physiologic reporting including heart rate, electrocardiographic changes, repolarization, ST or QRS changes in association with simultaneous or temporally connected respiratory skin bioimpedance or mechanical changes, thereby permitting the system to detect (e.g., and thrown an alert/alarm when identified) presence or withdrawal of drugs including methadone, heroin, amphetamine, alcohol, marijuana, LSD, caffeine or nicotine.

Figure 12:
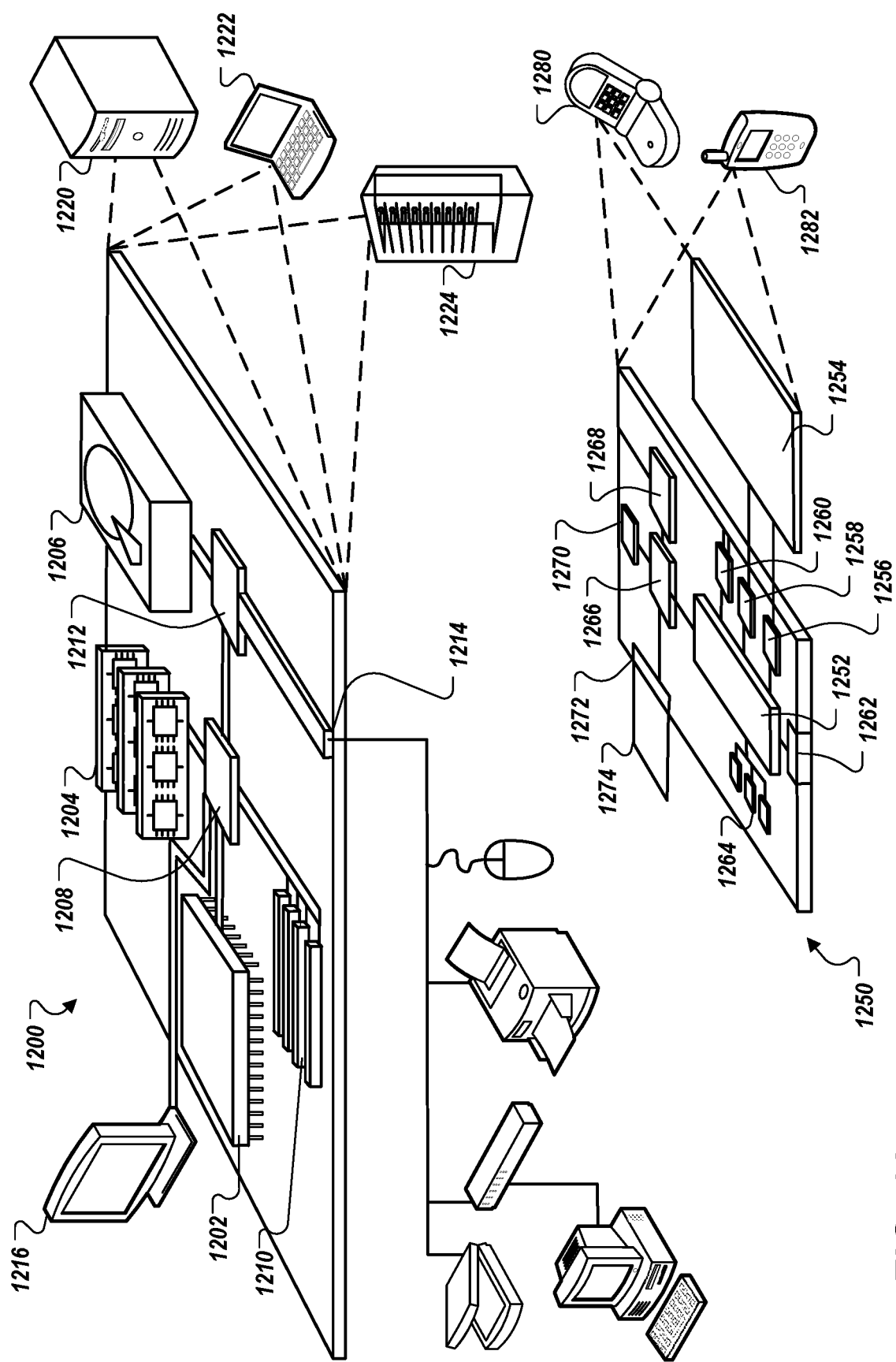
FIG. 12 shows an example of a computing device 1200 and a mobile computing device that may be applied to any of the computing systems and devices discussed herein. In some implementations, these devices in FIG. 12 may be configured to perform, in a system of one or more computers, the computer-implemented methods described herein.

FIG. 12 shows an example of a computing device 1200 and a mobile computing device that can be used to implement the techniques described herein. The computing device 1200 is intended to represent various forms of digital computers, such as laptops, desktops, workstations, personal digital assistants, servers, blade servers, mainframes, and other appropriate computers. The mobile computing device is intended to represent various forms of mobile devices, such as personal digital assistants, cellular telephones, smart-phones, and other similar computing devices. The components shown here, their connections and relationships, and their functions, are meant to be exemplary only, and are not meant to limit implementations of the inventions described and/or claimed in this document.

The computing device 1200 includes a processor 1202, a memory 1204, a storage device 1206, a high-speed interface 1208 connecting to the memory 1204 and multiple high-speed expansion ports 1210, and a low-speed interface 1212 connecting to a low-speed expansion port 1214 and the storage device 1206. Each of the processor 1202, the memory 1204, the storage device 1206, the high-speed interface 1208, the high-speed expansion ports 1210, and the low-speed interface 1212, are interconnected using various busses, and may be mounted on a common motherboard or in other manners as appropriate. The processor 1202 can process instructions for execution within the computing device 1200, including instructions stored in the memory 1204 or on the storage device 1206 to display graphical information for a GUI on an external input/output device, such as a display 1216 coupled to the high-speed interface 1208. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 1204 stores information within the computing device 1200. In some implementations, the memory 1204 is a volatile memory unit or units. In some implementations, the memory 1204 is a non-volatile memory unit or units. The memory 1204 may also be another form of computer-readable medium, such as a magnetic or optical disk.

The storage device 1206 is capable of providing mass storage for the computing device 1200. In some implementations, the storage device 1206 may be or contain a computer-readable medium, such as a floppy disk device, a hard disk device, an optical disk device, or a tape device, a flash memory or other similar solid state memory device, or an array of devices, including devices in a storage area network or other configurations. The computer program product may also contain instructions that, when executed, perform one or more methods, such as those described above. The computer program product can also be tangibly embodied in a computer- or machine-readable medium, such as the memory 1204, the storage device 1206, or memory on the processor 1202.

The high-speed interface 1208 manages bandwidth-intensive operations for the computing device 1200, while the low-speed interface 1212 manages lower bandwidth-intensive operations. Such allocation of functions is exemplary only. In some implementations, the high-speed interface 1208 is coupled to the memory 1204, the display 1216 (e.g., through a graphics processor or accelerator), and to the high-speed expansion ports 1210, which may accept various expansion cards (not shown). In the implementation, the low-speed interface 1212 is coupled to the storage device 1206 and the low-speed expansion port 1214. The low-speed expansion port 1214, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 1200 may be implemented in a number of different forms, as shown in the figure. For example, it may be implemented as a standard server 1220, or multiple times in a group of such servers. In addition, it may be implemented in a personal computer such as a laptop computer 1222. It may also be implemented as part of a rack server system 1224. Alternatively, components from the computing device 1200 may be combined with other components in a mobile device (not shown), such as a mobile computing device 1250. Each of such devices may contain one or more of the computing device 1200 and the mobile computing device 1250, and an entire system may be made up of multiple computing devices communicating with each other.

The mobile computing device 1250 includes a processor 1252, a memory 1264, an input/output device such as a display 1254, a communication interface 1266, and a transceiver 1268, among other components. The mobile computing device 1250 may also be provided with a storage device, such as a micro-drive or other device, to provide additional storage. Each of the processor 1252, the memory 1264, the display 1254, the communication interface 1266, and the transceiver 1268, are interconnected using various buses, and several of the components may be mounted on a common motherboard or in other manners as appropriate.

The processor 1252 can execute instructions within the mobile computing device 1250, including instructions stored in the memory 1264. The processor 1252 may be implemented as a chipset of chips that include separate and multiple analog and digital processors. The processor 1252 may provide, for example, for coordination of the other components of the mobile computing device 1250, such as control of user interfaces, applications run by the mobile computing device 1250, and wireless communication by the mobile computing device 1250.

The processor 1252 may communicate with a user through a control interface 1258 and a display interface 1256 coupled to the display 1254. The display 1254 may be, for example, a TFT (Thin-Film-Transistor Liquid Crystal Display) display or an OLED (Organic Light Emitting Diode) display, or other appropriate display technology. The display interface 1256 may comprise appropriate circuitry for driving the display 1254 to present graphical and other information to a user. The control interface 1258 may receive commands from a user and convert them for submission to the processor 1252. In addition, an external interface 1262 may provide communication with the processor 1252, so as to enable near area communication of the mobile computing device 1250 with other devices. The external interface 1262 may provide, for example, for wired communication in some implementations, or for wireless communication in other implementations, and multiple interfaces may also be used.

The memory 1264 stores information within the mobile computing device 1250. The memory 1264 can be implemented as one or more of a computer-readable medium or media, a volatile memory unit or units, or a non-volatile memory unit or units. An expansion memory 1274 may also be provided and connected to the mobile computing device 1250 through an expansion interface 1272, which may include, for example, a SIMM (Single In Line Memory Module) card interface. The expansion memory 1274 may provide extra storage space for the mobile computing device 1250, or may also store applications or other information for the mobile computing device 1250. Specifically, the expansion memory 1274 may include instructions to carry out or supplement the processes described above, and may include secure information also. Thus, for example, the expansion memory 1274 may be provide as a security module for the mobile computing device 1250, and may be programmed with instructions that permit secure use of the mobile computing device 1250. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. The computer program product contains instructions that, when executed, perform one or more methods, such as those described above. The computer program product can be a computer- or machine-readable medium, such as the memory 1264, the expansion memory 1274, or memory on the processor 1252. In some implementations, the computer program product can be received in a propagated signal, for example, over the transceiver 1268 or the external interface 1262.

The mobile computing device 1250 may communicate wirelessly through the communication interface 1266, which may include digital signal processing circuitry where necessary. The communication interface 1266 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 1268 using a radio-frequency. In addition, short-range communication may occur, such as using a Bluetooth, WiFi, or other such transceiver (not shown). In addition, a GPS (Global Positioning System) receiver module 1270 may provide additional navigation- and location-related wireless data to the mobile computing device 1250, which may be used as appropriate by applications running on the mobile computing device 1250.

The mobile computing device 1250 may also communicate audibly using an audio codec 1260, which may receive spoken information from a user and convert it to usable digital information. The audio codec 1260 may likewise generate audible sound for a user, such as through a speaker, e.g., in a handset of the mobile computing device 1250. Such sound may include sound from voice telephone calls, may include recorded sound (e.g., voice messages, music files, etc.) and may also include sound generated by applications operating on the mobile computing device 1250.

The mobile computing device 1250 may be implemented in a number of different forms, as shown in the figure. For example, it may be implemented as a cellular telephone 1280. It may also be implemented as part of a smart-phone 1282, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In situations in which the systems, methods, devices, and other techniques here collect personal information (e.g., context data) about users, or may make use of personal information, the users may be provided with an opportunity to control whether programs or features collect user information (e.g., information about a user's social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

Although various implementations have been described in detail above, other modifications are possible. In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

What is claimed is:

1. A computer-implemented method, comprising:
   obtaining, by a system of one or more computers, a maternal electrocardiogram (ECG) signal that represents an ECG of a pregnant mother during a first time interval, wherein the maternal ECG signal is acquired from one or more electrodes affixed to at least one of an abdominal region of the mother or a chest region of the mother;
   obtaining, by the system, a mixed maternal-fetal ECG signal that represents a combined ECG of the mother and her fetus during the first time interval, wherein the mixed maternal-fetal ECG signal is acquired from one or more electrodes of a vaginal probe located within a vaginal canal of the mother;
   processing, by the system, the maternal ECG signal and the mixed maternal-fetal ECG signal to generate a fetal ECG signal that represents the ECG of the fetus during the time interval, the fetal ECG signal substantially excluding the maternal ECG signal; and
   providing, by the system, an output based on the fetal ECG signal.

2. The computer-implemented method of claim 1, wherein the system comprises a smartphone or a tablet computing device.

3. The computer-implemented method of claim 1, further comprising synchronizing the maternal ECG signal with the mixed maternal-fetal ECG signal.

4. The computer-implemented method of claim 1, wherein processing the maternal ECG signal and the mixed maternal-fetal ECG signal to generate the fetal ECG signal comprises subtracting the maternal ECG signal from the mixed maternal-fetal ECG signal to generate the fetal ECG signal.

5. The computer-implemented method of claim 1, further comprising applying an adaptive filter to the maternal ECG signal before subtracting the maternal ECG signal from the mixed maternal-fetal ECG signal.

6. The computer-implemented method of claim 1, wherein the adaptive filter comprises a Wiener filter.

7. The computer-implemented method of claim 1, wherein processing the maternal ECG signal and the mixed maternal-fetal ECG signal to generate the fetal ECG signal comprises using a blind source separation technique to separate the fetal ECG signal from the maternal ECG signal.

8. The computer-implemented method of claim 1, wherein processing the maternal ECG signal and the mixed maternal-fetal ECG signal to generate the fetal ECG signal comprises using at least one of principal component analysis (PCA) or independent component analysis (ICA) techniques.

9. The computer-implemented method of claim 1, further comprising analyzing the fetal ECG signal to determine a distress level of the fetus; and wherein providing the output comprises generating an alert for presentation to a human user in response to a determination that the determined distress level of the fetus exceeds a threshold distress level.

10. A computer-implemented method, comprising:
    receiving, by a system of one or more computers, a first ECG signal, wherein the first ECG signal is a mixed maternal-fetal ECG signal that represents a combined ECG of a pregnant mother and her fetus, wherein the mixed maternal-fetal ECG signal was acquired using one or more electrodes from within a vaginal canal of the mother;
    processing, by the system, the first ECG signal to determine values for one or more features of the first ECG signal;
    determining, based on the determined values for the one or more features of the first ECG signal, a condition of at least one of the mother or the fetus; and
    providing, by the system, an output based on the determined condition of the at least one of the mother or the fetus.

11. The computer-implemented method of claim 10, wherein the features of the first ECG signal comprise features of a waveform for a beat from the first ECG signal, the features of the waveform including a slope or an area of a portion of the waveform for the beat.

12. The computer-implemented method of claim 10, wherein determining the condition of the at least one of the mother or the fetus comprises accessing a model that correlates at least one of maternal conditions or fetal conditions with ECG signal features.

13. The computer-implemented method of claim 12, wherein the model comprises an artificial neural network.

14. A vaginal probe for sensing information about a patient from within a vaginal canal of the patient, the probe comprising:
    a ring-shaped body structured and dimensioned for placement within the vaginal canal of the patient;
    a set of ECG sensors comprising one or more electrodes disposed on the ring-shaped body, the set of ECG sensors configured to abut walls of the vaginal canal when the ring-shaped body is placed within the vaginal canal of the patient, the set of ECG sensors configured to detect a maternal ECG signal if the patient is not pregnant or to detect a mixed maternal-fetal ECG signal if the patient is pregnant in at least the second or third trimesters;
    a wireless communications interface configured to wirelessly transmit RF signals that encode information about the maternal ECG signal or the mixed maternal-fetal ECG signal; and
    a controller configured to activate or deactivate ECG signal acquisition and transmission.

15. The vaginal probe of claim 14, further comprising at least one of a temperature sensor, a pH sensor, an accelerometer, a gyroscope, electromyography (EMG) sensors, or electrochemical sensors.

16. The vaginal probe of claim 14, wherein the ring-shaped body is made of a nitinol alloy.

17. The vaginal probe of claim 14, further comprising an induction coil that is configured to energize the vaginal probe when an external inductive power source is brought into proximity of the induction coil of the vaginal probe.

* * * * *